United States Patent
Ryu et al.

(10) Patent No.: US 9,566,173 B2
(45) Date of Patent: Feb. 14, 2017

(54) MOTION CONTROL DEVICE BASED ON WINDING STRING

(71) Applicant: KOREA UNIVERSITY OF TECHNOLOGY AND EDUCATION INDUSTRY-UNIVERSITY COOPERATION FOUNDATION, Cheonan-si (KR)

(72) Inventors: Jee Hwan Ryu, Cheonan-si (KR); Dmitry Popov, Cheonan-si (KR); Igor Gaponov, Cheonan-si (KR)

(73) Assignee: KOREA UNIVERSITY OF TECHNOLOGY AND EDUCATION INDUSTRY-UNIVERSITY COOPERATION FOUNDATION (KR)

( * ) Notice: Subject to any disclaimer, the term of this patent is extended or adjusted under 35 U.S.C. 154(b) by 0 days.

(21) Appl. No.: 14/419,037

(22) PCT Filed: Jul. 30, 2013

(86) PCT No.: PCT/KR2013/006822
§ 371 (c)(1),
(2) Date: Feb. 24, 2015

(87) PCT Pub. No.: WO2014/021603
PCT Pub. Date: Feb. 6, 2014

(65) Prior Publication Data
US 2015/0190246 A1    Jul. 9, 2015

(30) Foreign Application Priority Data

Aug. 2, 2012  (KR) .................. 10-2012-0084828
Mar. 11, 2013 (KR) .................. 10-2013-0025412
May 15, 2013  (KR) .................. 10-2013-0055325

(51) Int. Cl.
*F16H 27/02* (2006.01)
*A61F 2/54* (2006.01)
(Continued)

(52) U.S. Cl.
CPC ............. *A61F 2/54* (2013.01); *A61F 5/013* (2013.01); *A61H 1/0285* (2013.01);
(Continued)

(58) Field of Classification Search
CPC .......... A61F 2/54; A61F 5/013; A61H 1/0285; A61H 1/0288; B25J 9/0006; B25J 9/104; B25J 13/02; B25J 13/025; B25J 15/10
(Continued)

(56) References Cited

U.S. PATENT DOCUMENTS 4,921,293 A * 5/1990 Ruoff ............. A61F 2/583
                                                 294/106
4,986,280 A * 1/1991 Marcus ........... A61B 5/103
                                                 33/512
(Continued)

FOREIGN PATENT DOCUMENTS

JP    07204233    8/1995
JP    2008196566  8/2008
(Continued)

OTHER PUBLICATIONS

International Search Report—PCT/KR2013/006822 dated Aug. 27, 2013.

*Primary Examiner* — William Kelleher
*Assistant Examiner* — Zakaria Elahmadi
(74) *Attorney, Agent, or Firm* — Cantor Colburn LLP

(57) ABSTRACT

Provided is a motion control device. The device comprises one or more frames which supports an exoskeleton of a body; a string which connects the frames with each other; a pulley which is disposed between the frames and connected (Continued)

to one end of the string; and a motor which is connected to the other end of the string to control the string, wherein the pulley rotates the string according to control of the motor.

5 Claims, 15 Drawing Sheets

(51) Int. Cl.
B25J 9/00 (2006.01)
B25J 9/10 (2006.01)
B25J 13/02 (2006.01)
A61F 5/01 (2006.01)
G06F 3/01 (2006.01)
A61H 1/02 (2006.01)
B25J 15/10 (2006.01)

(52) U.S. Cl.
CPC .......... *A61H 1/0288* (2013.01); *B25J 9/0006* (2013.01); *B25J 9/104* (2013.01); *B25J 13/02* (2013.01); *B25J 13/025* (2013.01); *B25J 15/10* (2013.01); *G06F 3/011* (2013.01); *G06F 3/014* (2013.01); *A61F 2002/543* (2013.01); *A61H 2201/1215* (2013.01); *A61H 2201/165* (2013.01); *A61H 2201/1638* (2013.01); *A61H 2201/1676* (2013.01); *Y10S 901/36* (2013.01); *Y10T 74/18848* (2015.01)

(58) Field of Classification Search
USPC ......... 74/490.01–490.09; 294/111, 106, 907; 600/595; 606/1, 130; 901/36
See application file for complete search history.

(56) References Cited

U.S. PATENT DOCUMENTS

| | | | | |
|---|---|---|---|---|
| 5,062,673 A * | 11/1991 | Mimura | ............... | B25J 15/0009 294/106 |
| 5,080,682 A * | 1/1992 | Schectman | ............ | A61F 2/583 294/111 |
| 5,316,017 A * | 5/1994 | Edwards | ................ | G06F 3/014 600/595 |
| 5,447,403 A * | 9/1995 | Engler, Jr. | ........... | B25J 15/0009 294/111 |
| 5,587,937 A * | 12/1996 | Massie | .................. | B25J 9/1689 700/264 |
| 5,631,861 A * | 5/1997 | Kramer | .................... | B25J 13/02 414/5 |
| 6,042,555 A * | 3/2000 | Kramer | .................. | A61B 5/225 600/595 |
| 6,104,379 A * | 8/2000 | Petrich | .................... | G06F 3/011 345/156 |
| 6,110,130 A * | 8/2000 | Kramer | ................ | A61B 5/1071 600/587 |
| 7,410,338 B2 * | 8/2008 | Schiele | ................ | A61H 1/0274 414/4 |
| 7,673,916 B2 * | 3/2010 | Greenhill | ............. | B25J 15/0009 294/106 |
| 8,054,289 B2 * | 11/2011 | Berkley | .................. | G06F 3/016 345/156 |
| 8,056,423 B2 * | 11/2011 | Abdallah | ............... | B25J 9/1045 73/826 |
| 8,521,331 B2 * | 8/2013 | Itkowitz | ............. | A61B 19/2203 606/1 |
| 8,935,003 B2 * | 1/2015 | Itkowitz | ............. | A61B 19/2203 700/245 |
| 2003/0120183 A1 * | 6/2003 | Simmons | .................. | A61F 4/00 600/595 |
| 2005/0024331 A1 * | 2/2005 | Berkley | .................. | G06F 3/016 345/161 |
| 2008/0000317 A1 * | 1/2008 | Patton | .................. | A61F 5/0102 74/500.05 |
| 2008/0066574 A1 * | 3/2008 | Murata | ..................... | A61F 2/68 74/826 |
| 2011/0040408 A1 * | 2/2011 | De La Rosa Tames | .................... | B25J 9/1045 700/258 |
| 2014/0277739 A1 * | 9/2014 | Kornbluh | ............... | B25J 9/0006 700/260 |
| 2015/0209214 A1 * | 7/2015 | Herr | ........................ | A61H 3/00 623/27 |

FOREIGN PATENT DOCUMENTS

| | | |
|---|---|---|
| KR | 101011011 | 1/2011 |
| KR | 1020110104781 | 9/2011 |

* cited by examiner

Fig. 2
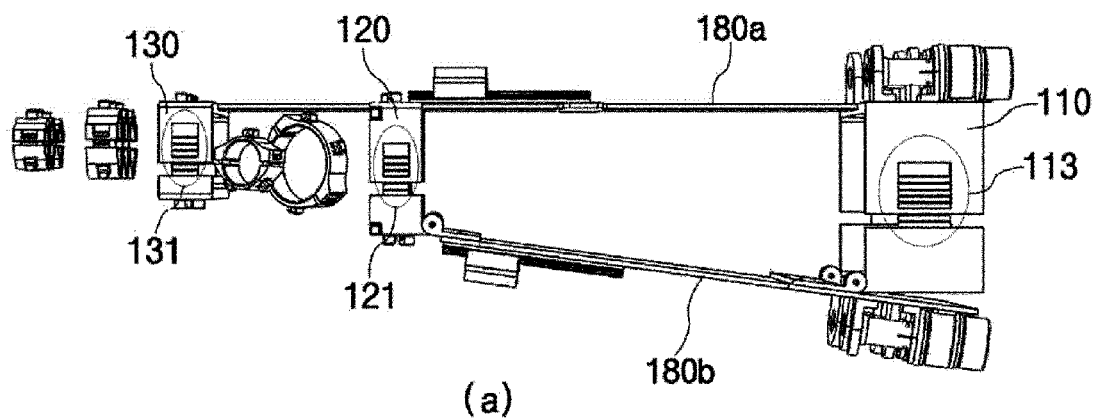
(a)
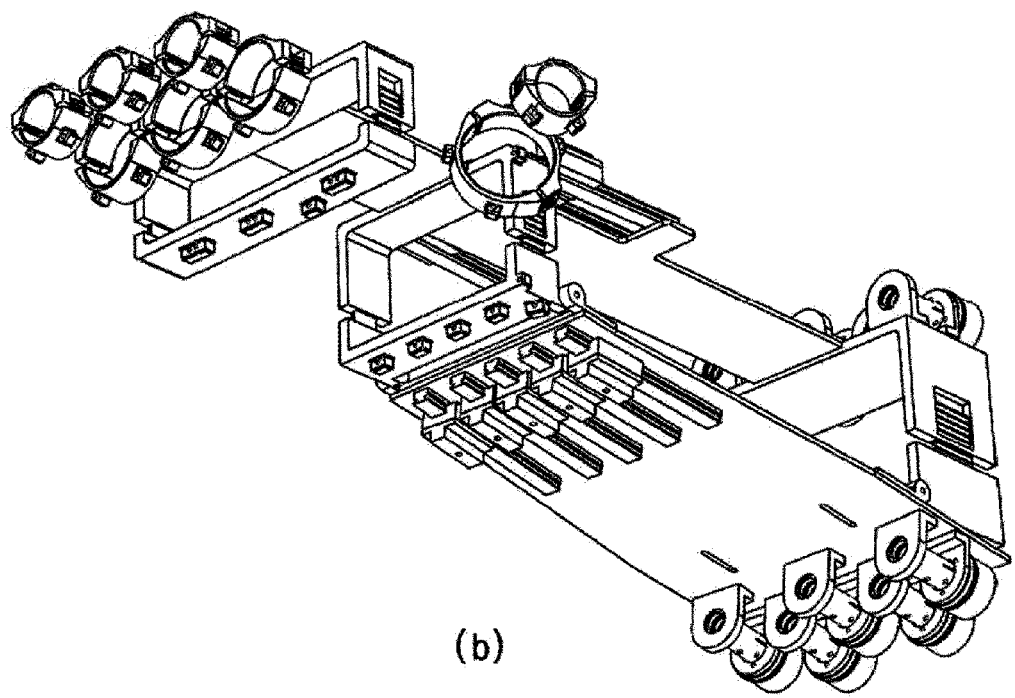
(b)

Fig. 6
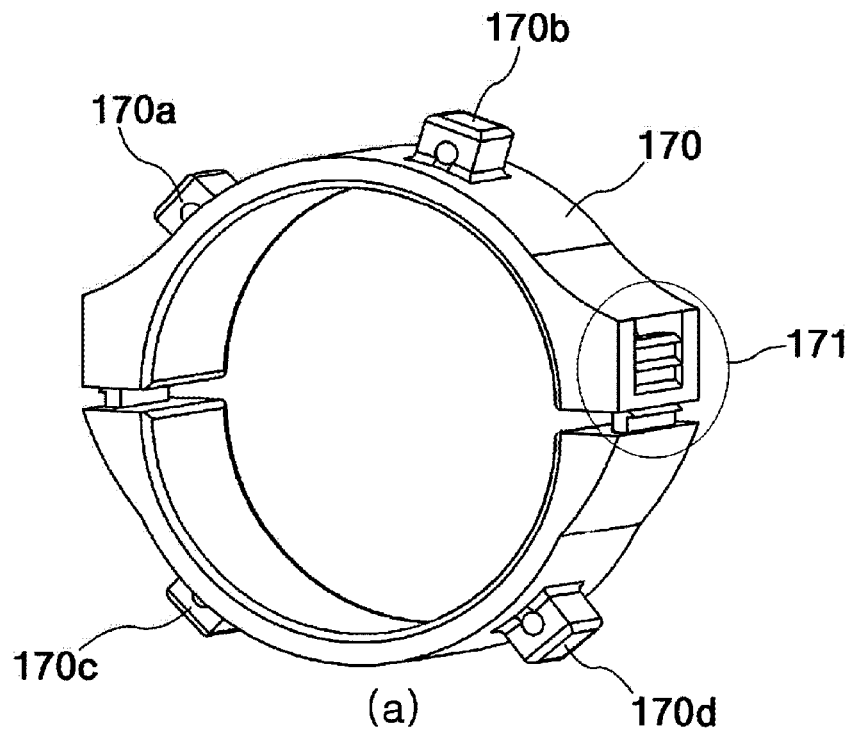
(a)
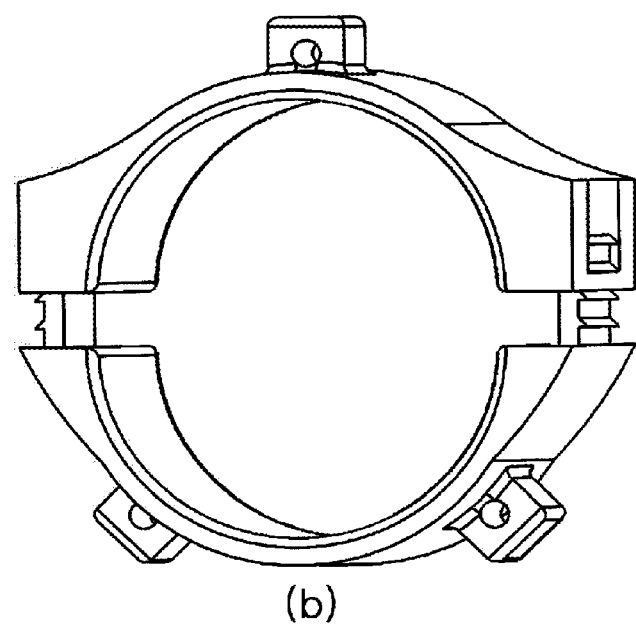
(b)

Fig. 12
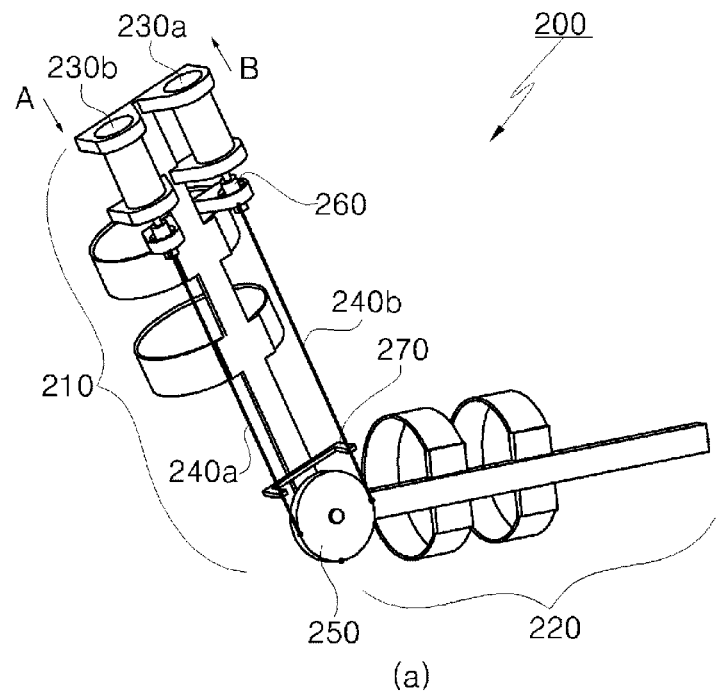
(a)
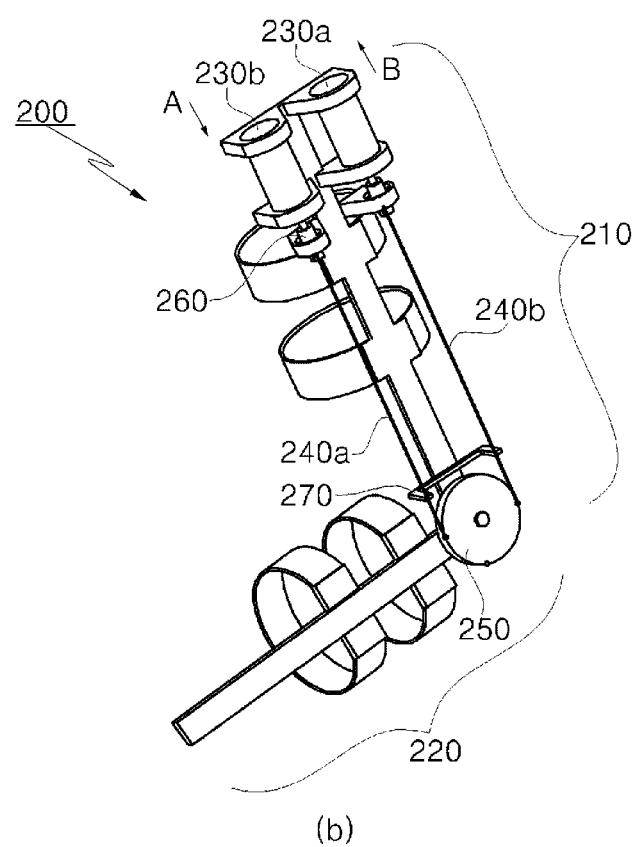
(b)

Fig. 13
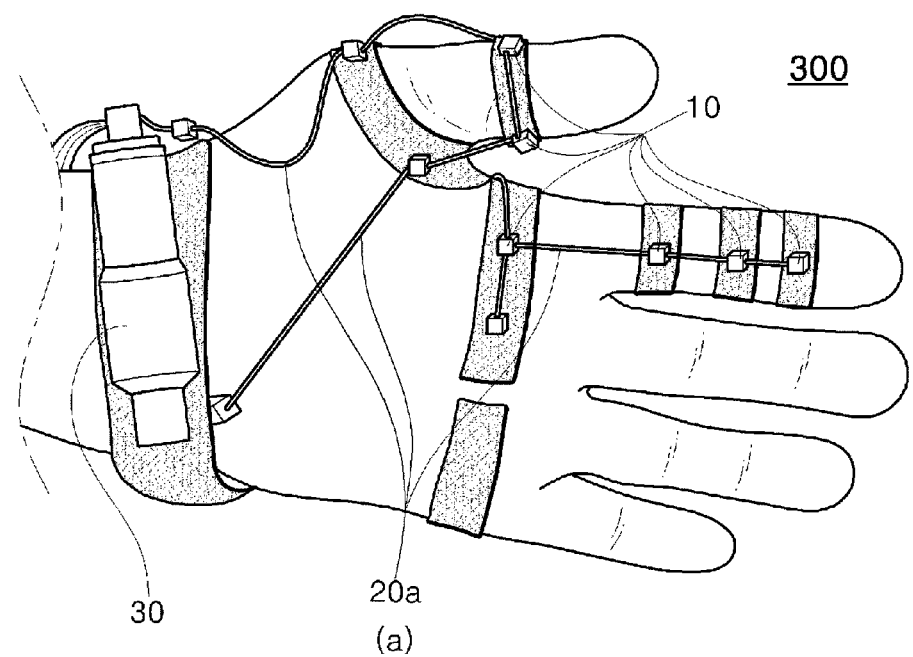
(a)
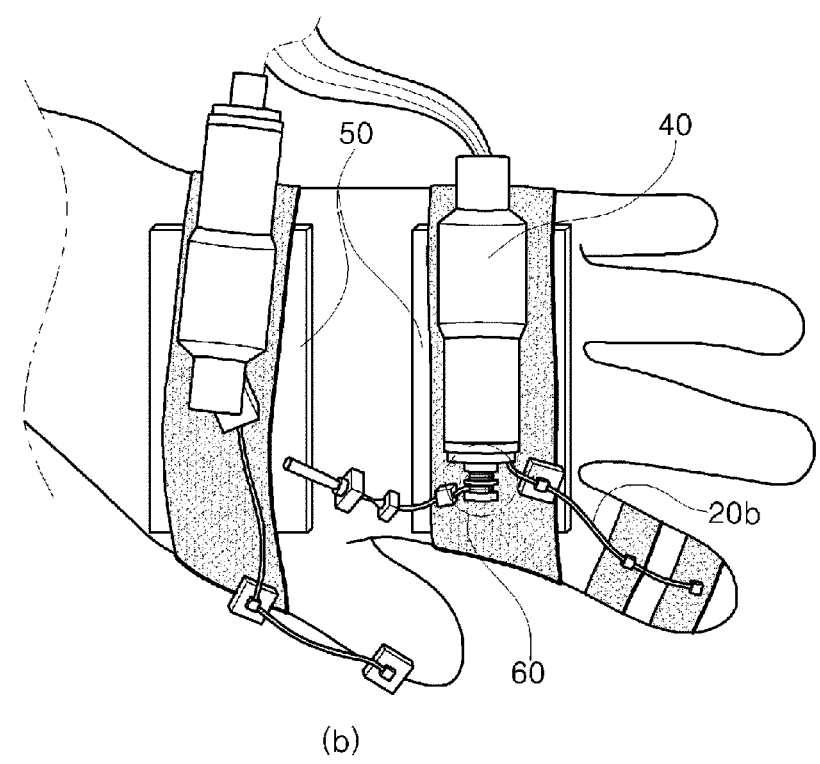
(b)

MOTION CONTROL DEVICE BASED ON WINDING STRING

CROSS-REFERENCE TO RELATED APPLICATION

This Application is a Section 371 National Stage Application of International Application No. PCT/KR2013/006822, filed Jul. 30, 2013, the contents of which are hereby incorporated by reference in its entirety.

BACKGROUND OF THE INVENTION

Technical Field

The present invention relates to a device for efficiently assisting the motion by utilizing the twisting of a string.

Background Art

In order to help a person who does not have a part of a body or cannot move a part of the body, a lot of auxiliaries in the wearing or mounting form have been developed. In particular, in order to help the person who cannot move the fingers, glove type wearing robots in the form of wearing by being put on the hands like a glove have been developed.

The conventional glove type wearing robot generally has an actuator which moves each joint of each finger using an exoskeleton structure for each joint, and has a sensor which detects the displacement or angle of motion of the joint.

As a result, when the actuator or the sensor is installed in a moving portion of the finger, the volume of the globe type wearing robot becomes increase and its weight also becomes heavy. There is a problem that the manufacturing cost also becomes very high due to such a complicated structure. Moreover, there are problems that the method of wearing and removing the glove becomes complicated, and despite the different sizes of the hands for each person, the glove size is defined.

However, the exoskeleton structure is a device designed to surround the specific regions of the body, and as the most serious drawback of all the current exoskeleton globes, when the actuator and the motor for moving the regions of the body are attached to the body, for its considerably large size, many exoskeleton type gloves have not been applied to a real life.

DISCLOSURE

Technical Problem

An aspect of the present invention provides a motion control device that can provide large force, by disposing a frame for supporting an exoskeleton of a body and by connecting the frames with a string to pull the string by a motor.

An aspect of the present invention provides a motion control device that can efficiently adjust the length of the string, by disposing a pulley for rotating the string in a joint part of the body.

An aspect embodiment of the invention provides a motion control device that can help the pulley to rotate with small force, by disposing a separator between the motor and the pulley when at least two strings are used, thereby allowing the untwisted string to wind around the pulley or allowing the untwisted string to unwind from the pulley.

An aspect of the present invention provides a motion control device that can provide large force even when using a small motor, by disposing a separator between the motor and the pulley, so that separator helps the pulley to rotate with a small force from the pulley of the untwisted string.

An aspect of the present invention provides a motion control device which enables the second frame to move in the different directions from each other by disposing the two motors and two strings.

An aspect of the present invention provides a motion control device which enables the string to wind around or unwind from the pulley according to the direction of motion of the motor, by disposing the motor for each region of the body to be moved and by disposing the pulley next to the motor so that the pulley rotates the string.

An aspect of the present invention provides a motion control device which can manually adjust the tension, by disposing a bolt and a nut to adjust the length of the string with the bolt and the nut, depending on the size of the body.

An aspect of the present invention provides a motion control device which can provide large force by utilizing a small motor, by directly disposing the motor in the glove and by pulling the string with the motor.

An aspect of the present invention provides a motion control device which makes the palms free to easily pick the object since the motor is attached to back of the hand and the wrist and is connected along the guide only with the string.

Technical Solution

According to an aspect of the present invention, there is provided a motion control device which includes one or more frames for supporting an exoskeleton of a body; a string for connecting the frames with each other; a pulley disposed between the frames and connected to one end of the string; and a motor connected to the other end of the string to control the string, wherein the pulley can rotate the string according to control of the motor.

Advantageous Effect

According to an embodiment of the present invention, it is possible to provide large force, by disposing a frame for supporting an exoskeleton of a body and by connecting the frames with a string to pull the string by a motor.

According to an embodiment of the present invention, it is possible to efficiently adjust the length of the string, by disposing a pulley for rotating the string in a joint part of the body.

According to an embodiment of the present invention, it is possible to help the pulley to rotate with small force, by disposing a separator between the motor and the pulley when at least two strings are used, thereby allowing the untwisted string to wind around the pulley or allowing the untwisted string to unwind from the pulley.

According to an embodiment of the present invention, it is possible to provide large force even when using a small motor, by disposing a separator between the motor and the pulley, so that the separator helps the pulley to rotate with a small force from the pulley of the untwisted string.

According to an embodiment of the present invention, it is possible to move the second frame in the different directions from each other by disposing the two motors and two strings.

According to an embodiment of the present invention, it is possible to enable the string to wind around or unwind from the pulley according to the direction of motion of the motor, by disposing the motor for each region of the body to be moved and by disposing the pulley next to the motor so that the pulley rotates the string.

According to an embodiment of the present invention, it is possible to manually adjust the tension, by disposing a bolt and a nut to adjust the length of the string with the bolt and the nut, depending on the size of the body.

According to an embodiment of the present invention, it is possible to provide large force by utilizing a small motor, by directly disposing the motor in the glove and by pulling the string with the motor.

According to an embodiment of the present invention, since the motor is attached to back of the hand and the wrist and is connected along the guide only with the string, the palms become free to easily pick the object.

BRIEF DESCRIPTION OF THE DRAWINGS

The above objects, other features and advantages of the present invention will become more apparent by describing the preferred embodiments thereof with reference to the accompanying drawings, in which:

FIG. 2 is a side view illustrating a side surface and a lower surface of the motion control device illustrated in FIG. 1.

FIG. 6 illustrates a joint included in the motion control device according to an embodiment of the present invention.

FIG. 12 is a block diagram illustrating a motion control device according to still another embodiment of the present invention.

FIG. 13 is a block diagram illustrating a motion control device according to still another embodiment of the present invention.

PREFERRED EMBODIMENTS OF THE INVENTION

The configuration and operation of the present invention will be described below in detail with reference to the accompanying drawings.

Figure 1:
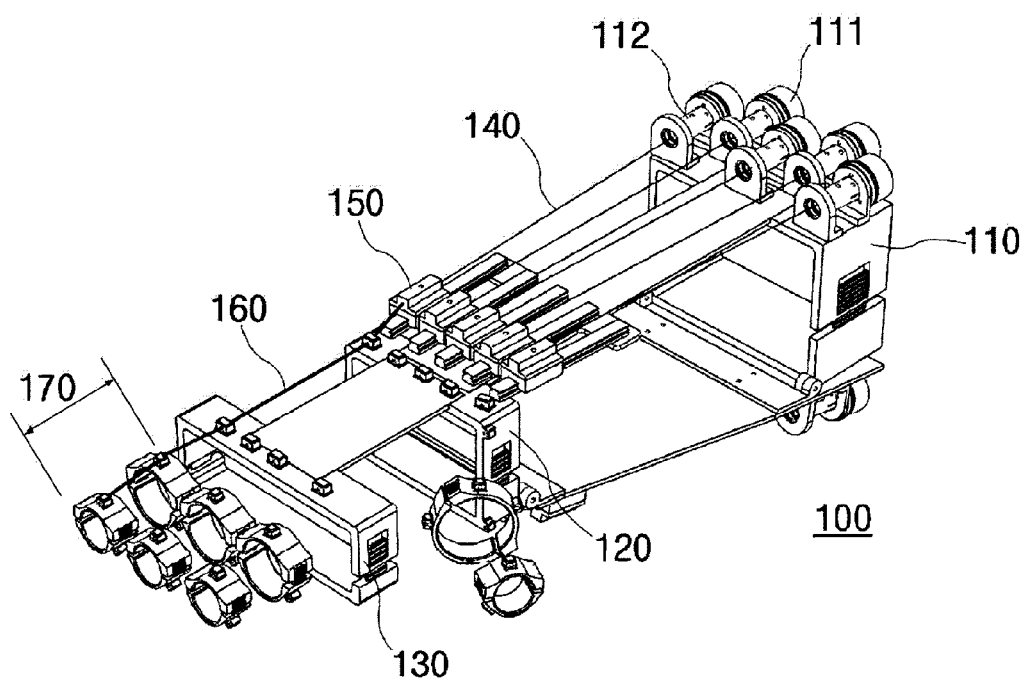
FIG. 1 is a block diagram illustrating a motion control device according to an embodiment of the present invention.

FIG. 1 is a block diagram illustrating a motion control device according to an embodiment of the present invention.

Referring to FIG. 1, the motion control device 100 according to the first embodiment includes one or more frames 110 to 130 that support an exoskeleton of a body, strings 140, 160 that connect between the frames 110 to 130, and a motor 111 that is connected to the strings 140, 160 to control the strings 140, 160.

The body is a concept that includes person, animal and robot having movable parts. In general, in order to move the body, it is necessary to have the exoskeleton around the joint. In FIG. 1, the body is defined as "person", and the frames are described as being formed in the person exoskeleton.

For example, the frames 110 to 130 can be configured to include a forearm frame 110 for supporting an exoskeleton of a mid forearm, a wrist frame 120 for supporting an exoskeleton of a wrist, and a palm frame 130 for supporting an exoskeleton of a palm.

The person's finger can be formed with a joint 170 which is formed of an elastic material to match the joints of the finger. Such a joint 170 is made of a flexible or elastic material so as to be able to be worn to match the user's fingers with the different sizes of hands, respectively. A connecting portion formed in the form of having two parts engaged with each other can be formed on the side surfaces of the joint 170.

The strings 140, 160 can be constituted by a first string 140 that connects the forearm frame 110 and the wrist frame 120, and a second string 160 that connects the wrist frame 120 and the palm frame 130. These strings 140, 160 are one or multiple twisted strings, and may be formed of an elastic material or an inextensible material. In this case, the string 240 can be either a twisted type or untwisted type.

One of the first string 140 is connected to the motor 111 by a first coupling 112 formed in the forearm frame 110 and can be twisted by the motor 111. The other side of the first string 140 can be connected to the second string 160 by a second coupling 150 formed in the wrist frame 120. The second string 160 can move the joint 170 and the connecting portion, according to the operation by the motor 111.

Rotation given to the first string 140 by the motor 111 reduces the length of the first string 140, and produces a linear motion from the viewpoint of a load. Thus, the formed motion control device 100 can be formed to have a small size, lightweight and the large tensile strength, by utilizing a very small and light electric motor 111 due to the reduction ratio of its own height (non-linearly).

The first coupling 112 and the second coupling 150 are intended to prevent the disconnection when the first string 140 or the second string 160 is twisted.

The motor 111 is formed in the forearm frame 110, operates so as to twist the first string 140, and pulls the second string 160 to control the person's fingers to move.

FIG. 2 is a side view illustrating a side surface and a lower surface of the motion control device illustrated in FIG. 1.

Referring to FIG. 2, on the side surface (a) of the frames 110 to 130 and the joint 170, connecting portions 113, 121, 131 can be formed in the form of having two parts engaged with each other. On sides of the connecting portions 113, 121, 131 are connected to the other sides in a manner capable of performing a rotational motion, and can be moved by the second string 160. The connecting portions 113, 121, 131 have a kind of guide mechanism, and the second string 160 is operated via the guide mechanism. The motion starts when force occurs at the end of the second string 160.

The connecting portions 113, 121, 131 are fixed to plates 180a, 180b. The connecting portions 113, 121, 131 and the plates 180a, 180b can provide a fixed reference value for every motion of the exoskeleton.

On the lower surface (b) of the frames 110 to 130 and the joint 170, similarly to the upper surface of FIG. 1, the first string 140, the second coupling 150 for connecting the first string and the second string 160, and the first coupling 112 for connecting the first string and the motor 111.

Figure 3:
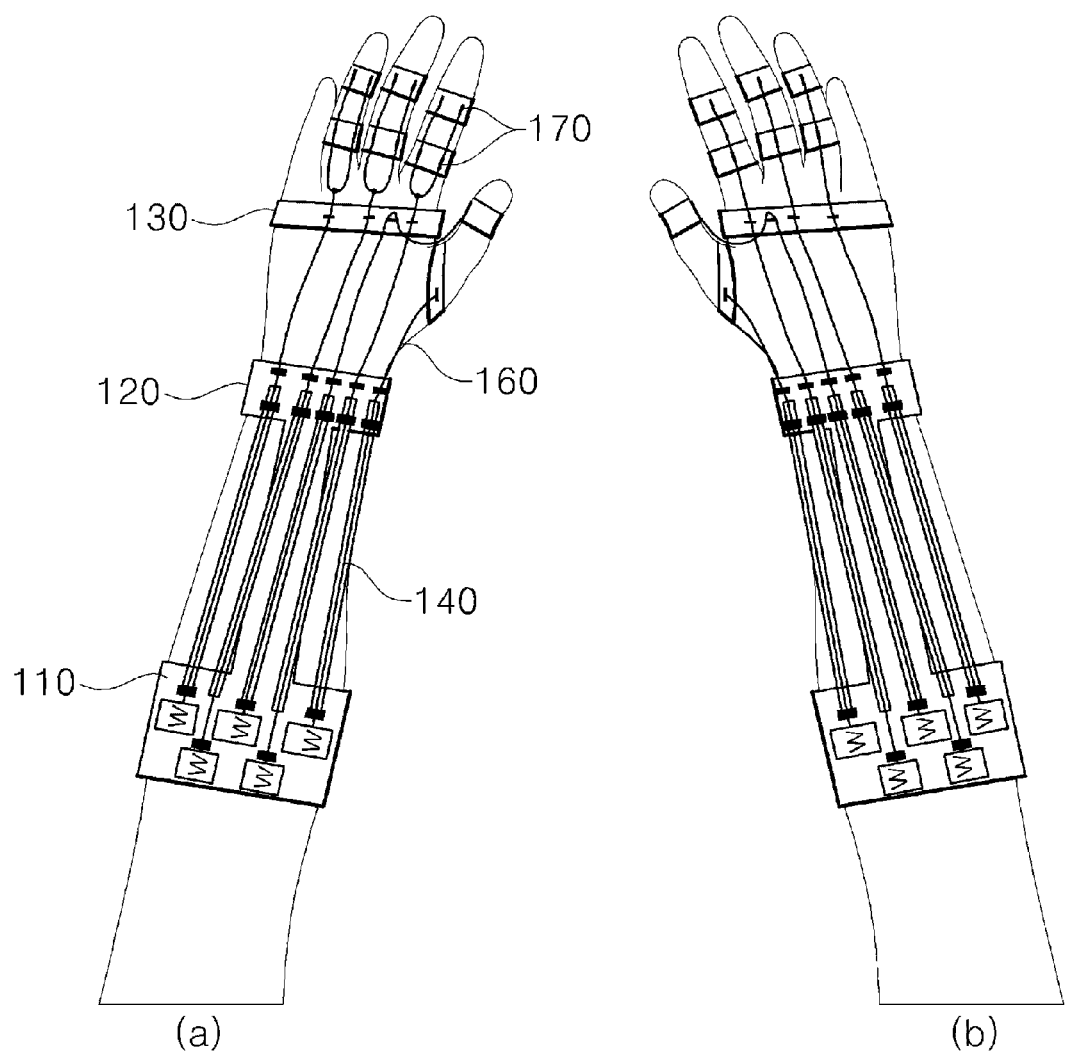
FIG. 3 is diagram illustrating the positions of each component of the motion control device when a person wears.

FIG. 3 is a diagram illustrating positions of each component of the motion control device when a person wears.

Referring to FIG. 3, (a) illustrates the position of the frames 110 to 130 which support an exoskeleton of a palm front of a person, and (b) illustrates the position the frames 110 to 130 which support an exoskeleton of a palm back of a person. That is, the motion control device of the present invention forms the frame 110 to 130 and the joint 170 which support central forearms, wrists, palms and fingers in front and back of a person's arm, and connects the frame 110 to 130 by the first string 140 or the second string 160, thereby being able to help a person to increase the force of the grasping operation.

Such an exoskeleton type glove can include an inner layer which is in direct contact with the human body, an intermediate layer which is formed outside the inner layer to assist the person's fingers to move by twist of the strings, and an outer skin layer which is formed so as to surround the intermediate layer.

The intermediate layer can include the frames 110 to 130 which support each of the forearms, the wrists and the palms of person illustrated in FIG. 1, the strings which connect the frames 110 or 130 to one another, and the motor which pulls the strings to perform the control so that the person's fingers are moved.

In an embodiment, twist technique can be applied to the strings 140, 160, depending on the flexor or extensor.

In order to make the light and portable motion control device, a string twist technique is applied, and the string twist technique can be used in imitation of the flexor and extensor muscles. For example, the first string 140 can be formed by the untwisted string in imitation of the flexor, and the second string 160 can be formed by the twisted string using the extensor. Alternatively, the first string 140 can be formed by the twisted string in imitation of the flexor, and the second string 160 can be formed by the twisted string in imitation of the extensor. Alternatively, both the first string and 140 the second string 160 may be formed by the twisted string.

In an embodiment, the inner layer may be formed of a soft material that is in direct contact with the human body. For example, the inner layer may be formed of any one of suede, velvet, silicon, urethane, leather or cotton.

In an embodiment, the outer skin layer is composed of any one of PVC (Polyvinyl chloride), aluminum and polar fleece, and can hold the shape of the exoskeleton type glove.

Figure 4:
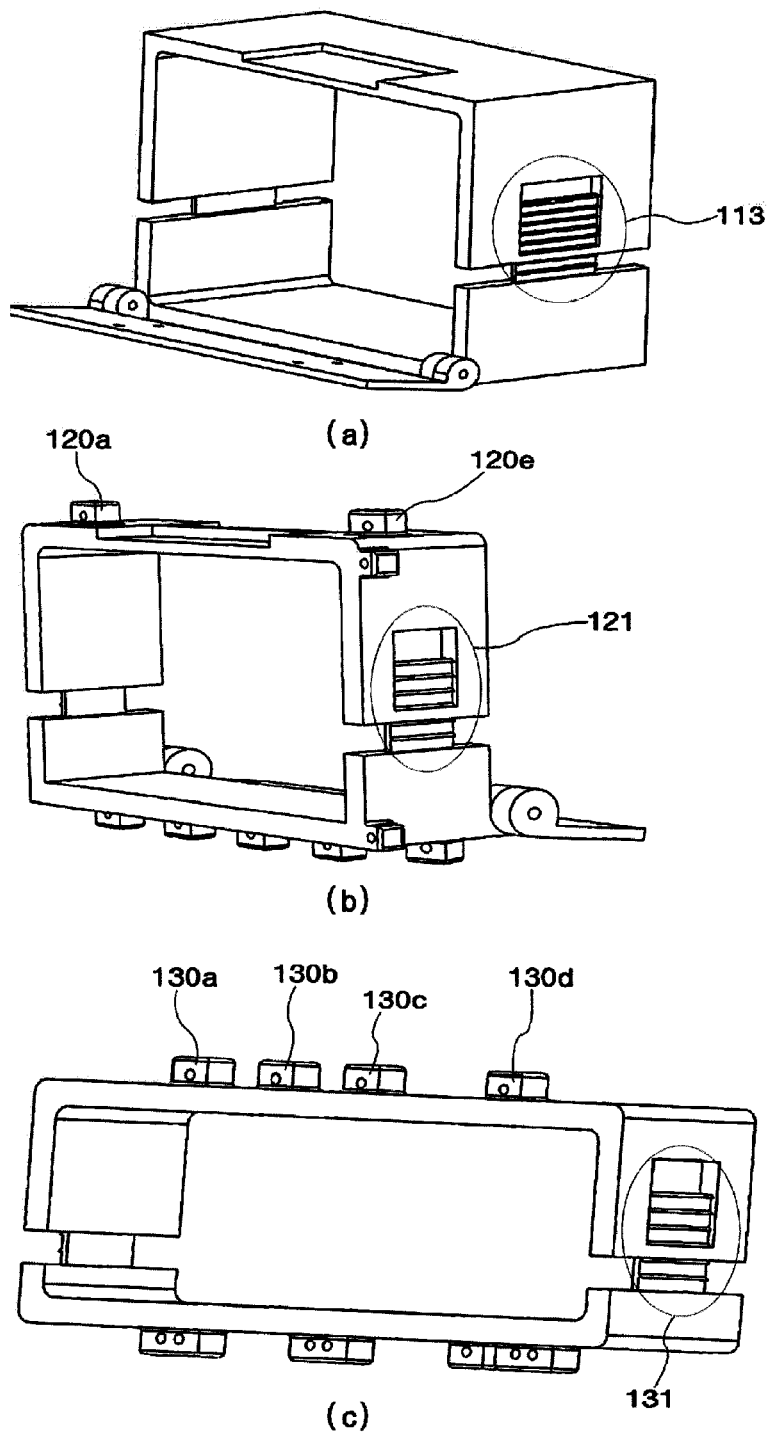
FIG. 4 is a diagram illustrating each frame included in the motion control device according to an embodiment of the present invention.

FIG. 4 is a diagram illustrating each frame included in the motion control device according to an embodiment of the present invention.

Referring to FIG. 4, (a) illustrates a forearm frame which serves to support the exoskeleton of the forearm. On the side of the forearm frame, a connecting portion 113 formed in the form of having two parts engaged with each other can be formed. When putting the exoskeleton type glove, the two engaged parts of the connecting portion 113 are significantly adjusted to be loosened, and when performing the operation of gripping with the fingers, the two parts are shortened by the pulling of the strings and can be tightened.

(b) illustrates a wrist frame which serves to support the exoskeleton of the wrist. Like the forearm frame, the connecting portion 121 can also be formed on the side of the wrist frame. Like the connecting portion 113 of (a), when putting the exoskeleton type globe, two engaged parts of the connecting portion 121 are significantly adjusted to be loosened, and when performing the operation of gripping with the fingers, the two parts are shortened by the pulling of the strings and can be tightened. Also, guides 120a, 120e for fixing the string to the wrist frame can be formed on the upper and lower surfaces of the wrist frame.

(c) illustrates a palm frame which serves to support the exoskeleton of the palm. Like the wrist frame, the connecting portion 131 can be formed on the side of the palm frame. Further, guides 130a to 130d for fixing the strings to the palm frame can be formed on the upper and lower surfaces of the palm frame.

Figure 5:
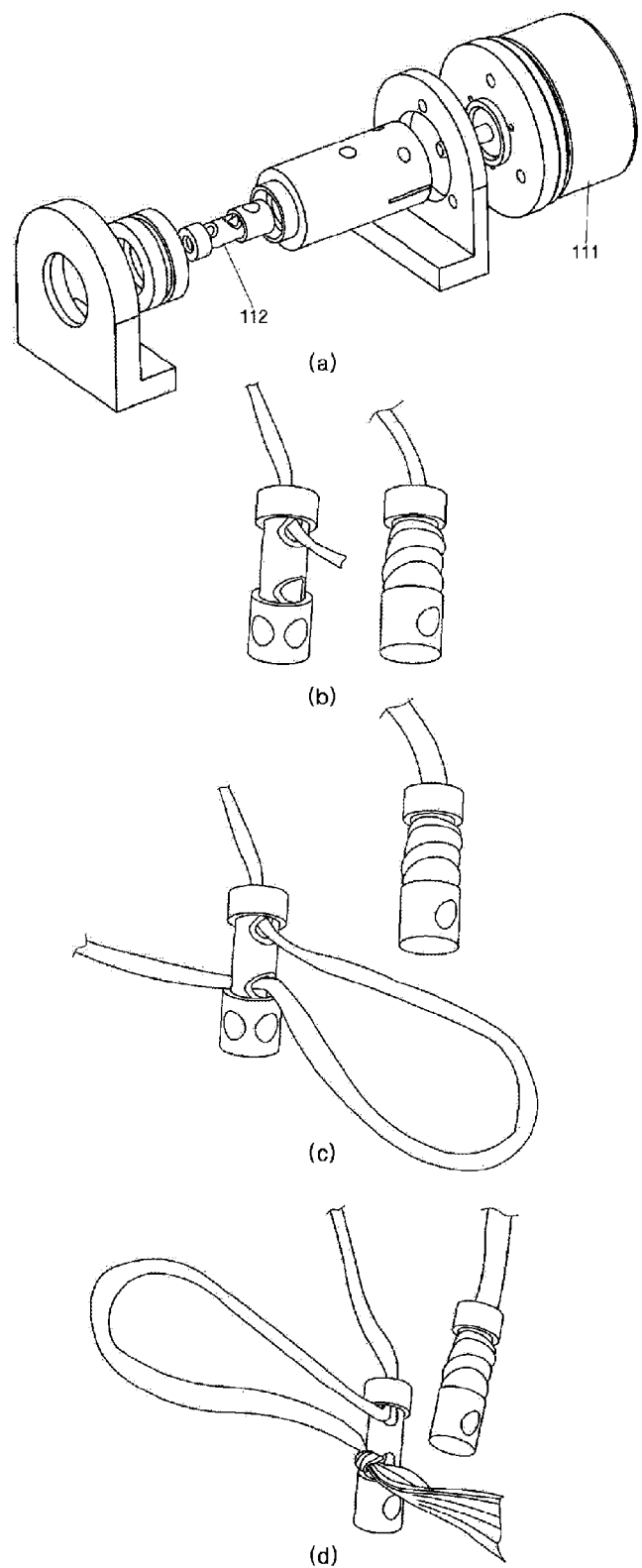
FIG. 5 is a diagram illustrating a coupling included in the motion control device according to an embodiment of the present invention.

FIG. 5 is a diagram illustrating a coupling that is included in the motion control device according to an embodiment of the present invention.

Referring to FIG. 5, the coupling 112 connects the string to the motor 111 to serve to fix the string (a). In other words, the coupling 112 is intended to prevent the string from breaking at the coupling end when the string is twisted.

The coupling 112 can be provided with a plurality of holes. In the present invention, since the string passes into the holes in the coupling 112 and the string winds around the coupling 112, even if the motor 111 pulls the string, the string can be prevented from breaking (b to d).

FIG. 6 is a diagram illustrating a joint that is included in the motion control device according to an embodiment of the present invention.

Referring to FIG. 6, the joint can be formed to match the joint of the person's finger. Each finger except the thumb provides one degree of freedom, but the thumb can provide two degrees of freedom.

Therefore, it is possible to classify the joint into a joint (a) which is formed to match the thumb's joint, and (b) a joint (b) which is formed to match the remaining four fingers. The joint (a) includes four guides to fix the second string, and the joint (b) can be formed with three guides.

For example, on the side of the joint (a or b), a connecting portion 171 formed in the form of having two parts engaged with each other can be formed. The number and degree of freedom of the joints and the connecting portions are variable and are dependent on the number of fingers.

Figure 7:
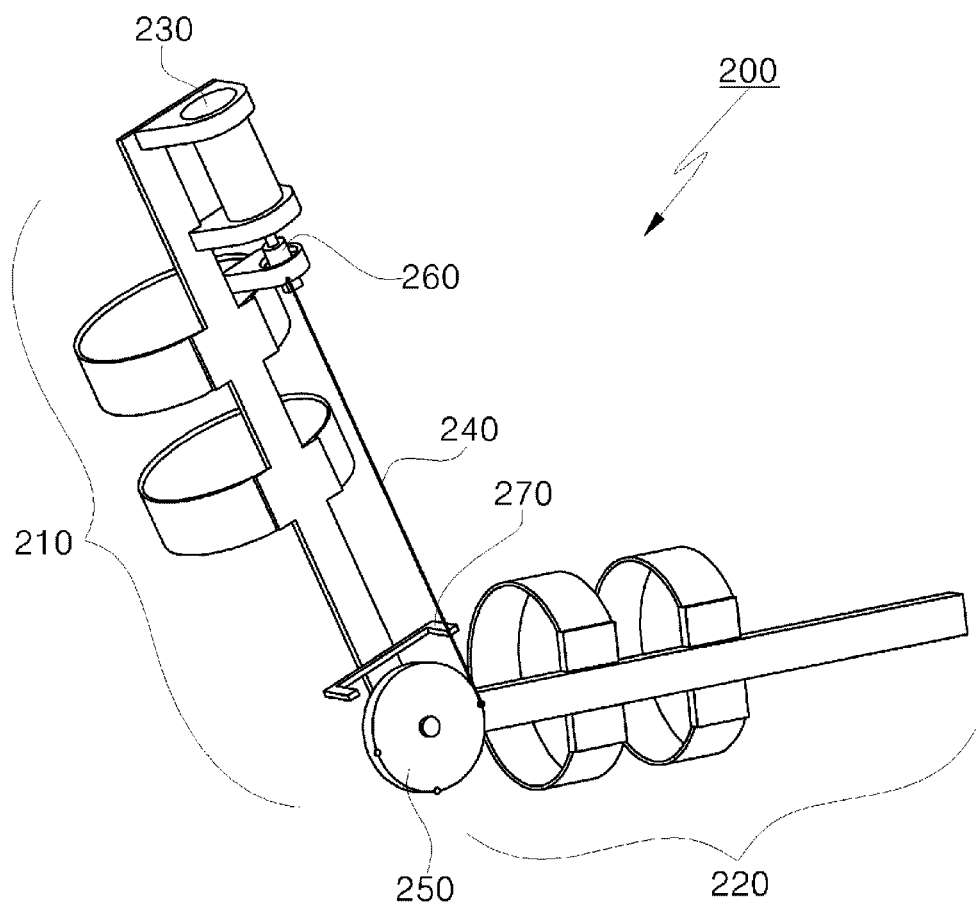
FIG. 7 is a block diagram illustrating a motion control device according to another embodiment of the present invention.

FIG. 7 is a block diagram illustrating a motion control device according to another embodiment of the present invention.

Referring to FIG. 7, a motion control device 200 of a second embodiment can include a first frame 210, a second frame portion 220, a motor 230, a string 240, a pulley 250, a coupling 260 and a separator 270.

The first frame 210 supports the upper exoskeleton of the body. For example, the first frame 210 is disposed on the exoskeleton located in an upper direction (sky direction) around the joint site of the body to be able to support the upper exoskeleton.

The second frame 220 supports the lower exoskeleton connected to the upper exoskeleton. For example, the second frame 220 is disposed in the exoskeleton positioned in a lower direction (ground surface direction) around the joint site of the body to be able to support the lower exoskeleton.

That is, the first frame 210 and the second frame 220 can be disposed at a site that moves in a predetermined direction based on the joint site of the body, respectively.

The string 240 connects the first frame 210 and the second frame 220 to each other.

In an embodiment, one end of the string 240 is connected to the motor 230 disposed in the first frame, and the other end different from the one end of the string 240 can be connected to a pulley 250 disposed between the first frame 210 and the second frame 220. Such a string 240 can be constituted by a single piece or at least two or more pieces.

The motor 230 is disposed in the first frame 210 to control the string 240. The motor 230 pulls the string 240 from the second frame 220 to enable the second frame 220 to move in the direction of the first frame 210 as the length of the string 240 is reduced.

The pulley 250 is disposed between the first frame 210 and the second frame 220 to be able to rotate the string 240 according to the control of the motor 230. The pulley 250 is a sheave that rotates the string 240.

Figure 8:
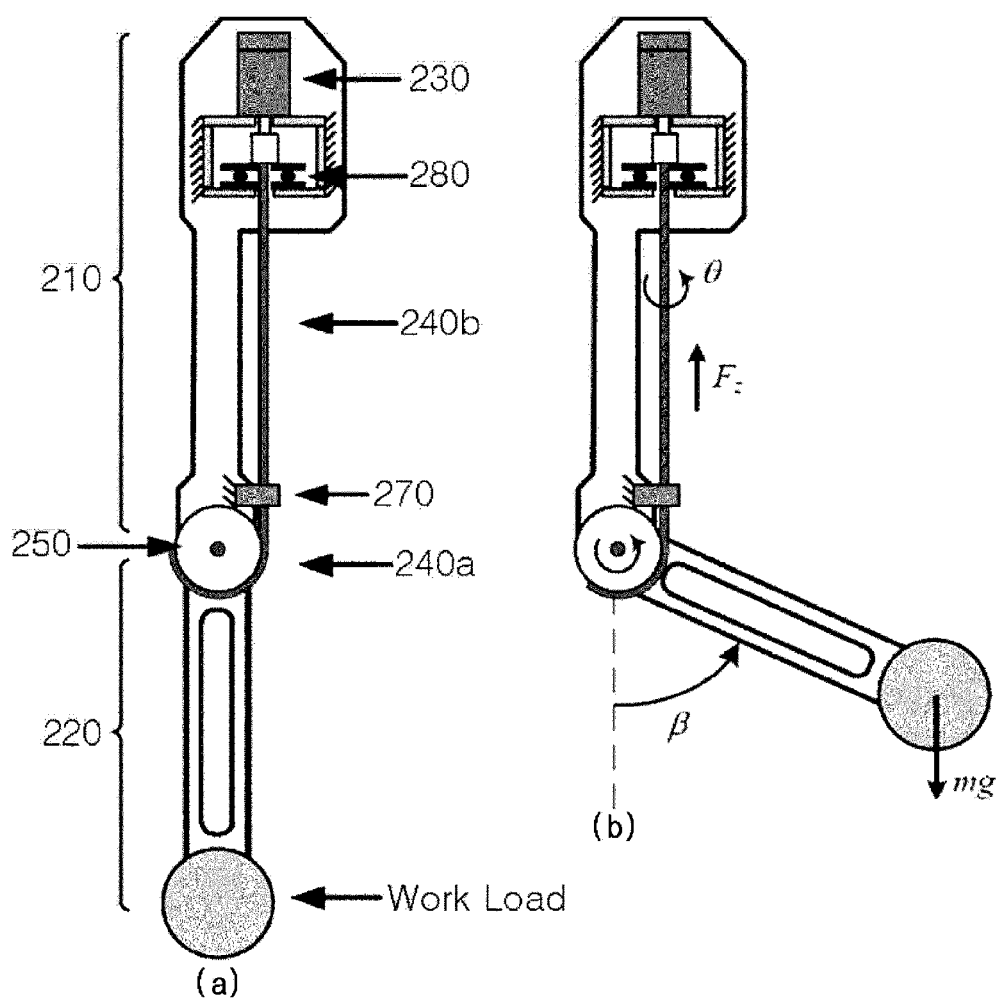
FIG. 8 is a diagram illustrating an example in which the components included in the motion control device according to another embodiment of the present invention are disposed in the body.

FIG. 8 is a diagram illustrating an example in which the components included in the motion control device according to another embodiment of the present invention are disposed in the body.

Referring to FIG. 8, the first frame 210 is disposed at the upper exoskeleton, the second frame 220 is disposed at the lower exoskeleton, and the pulley 250 can be disposed between the first frame 210 and the second frame 220. That is, the pulley 250 is disposed in the joint region of the body, the first frame 210 is disposed at one end of the pulley 250, and the second frame 220 is disposed at the other end of the pulley 250 opposite to the one end, thereby permitting the second frame 220 to move in a constant direction based on the joint region of the body.

For example, the string 240 is wound around the pulley 250 (a), and when the motor 230 pulls the string 240 in the direction of the motor 230, the second frame 220 moves in a β direction, while the string 240 wound around the pulley 250 is unwound along with the rotation of the pulley 250 (b). In contrast, when the motor 230 releases the pulled string 240, the second frame 220 moves in a direction opposite to the β direction, while the string 240 is wound around the pulley 250 along with the rotation of the pulley 250.

However, if there are at least two strings 240, when the string 240 is twisted or unwound after twisted, the strings 240 may be wound each other and the twisted string 240 may not be unwound. Therefore, in the present invention, if there are at least two strings 240, it is possible to include a separator 270 which is disposed between the motor 230 and the pulley 250 to separate the two or more strings 240.

Figure 9:
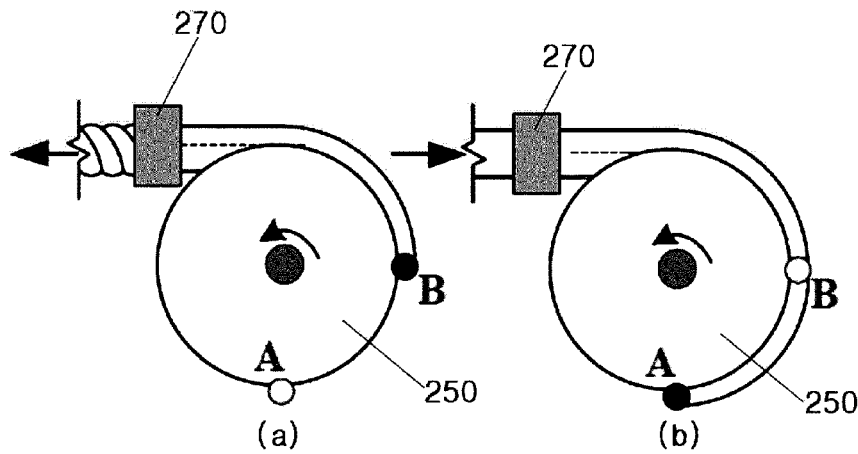
FIGS. 9 to 11 are diagrams illustrating an example of a separator included in the motion control device according to another embodiment of the present invention.
Figure 10:
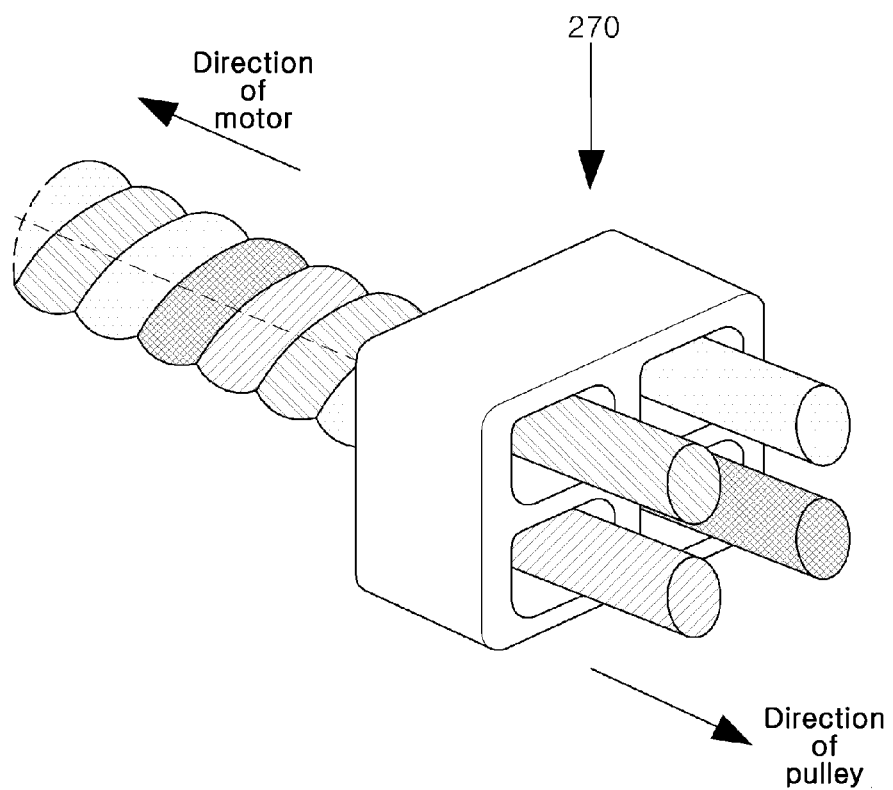
Figure 11:
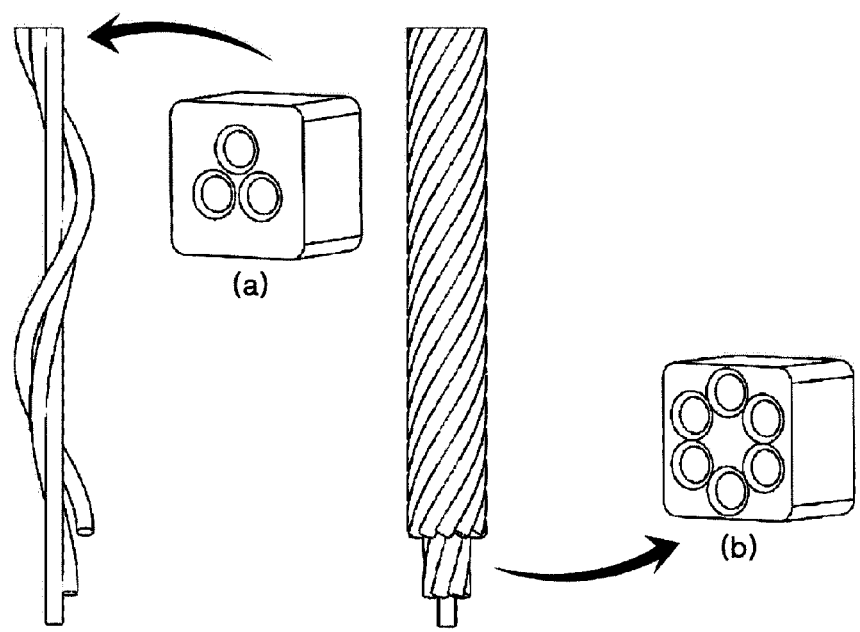

Referring to FIGS. 9 to 11 are diagrams illustrating an example of a separator included in a motion control device according to another embodiment of the present invention.

Referring to FIG. 9, the separator 270 can be disposed at a region before the string 240 is wound around the pulley 250. When the string 240 is completely unwound from the pulley 250, since the string 240 is twisted by the motor 230, the separator 270 makes the string 240 easier to be twisted (a). Also, if the string 240 is wound with the pulley 250, the separator 270 can unwind the twisted string 240 so that the twisted string 240 is untwisted and wound around the pulley 250 (b).

Referring to FIG. 10, the separator 270 can be used when at least two or more strings 240 are used.

Referring to FIG. 11, the separator 270 can be provided with the number of holes through which the string 240 passes in accordance with the number of the strings 240. That is, if three strings 240 are used, the separator 270 can be provided with three holes (a). Otherwise, if the six strings 240 are used, the separator 270 can be provided with six holes (b).

Thus, if at least two strings are used, the separator is disposed between the motor and the pulley so that the untwisted string is wound around the pulley or the untwisted string is unwound from the pulley, thereby being able to help the pulleys to rotate with small force. Therefore, since the separator helps the pulley to rotate with small force, it is possible to provide great force even when using a small motor.

FIG. 12 is a block diagram illustrating a motion control device according to another embodiment of the present invention.

Referring to (a) of FIG. 12, in a motion control device 200, a first frame 210 and a second frame 220 are each disposed at regions which move in a certain direction based on the joint region of the body, a pulley 250 is disposed between the first frame 210 and the second frame 220, and the device can include a first string 240a which is connected to the pulley 250 at one end and is connected to the first motor 230a at the other end different from the one end. At this time, the first motor 230a is disposed on the first frame 210 to pull the first string 240a from the pulley 250 to move the second frame 220.

However, the motion control device 200 can be provided with two motors and two strings. That is, the motion control device 200 can further include a second string 240b which is connected to the pulley 250 at one end and is connected to the second motor 230b at the other end different from the one end, and a second motor 230b which pulls the second string 240b from the pulley 250. At this time, if the motion control device 200 is provided with two motors and two strings, the two pulleys 250 and the two separators 270 disposed between the motors 230a, 230b and the pulleys 250 can also be provided. Thus, when there are at least two first strings 240a or second strings 240b, respectively, the separator 270 can separate each of the two or more first strings 240a or second strings 240b.

In this case, referring to (b) of FIG. 12, the second motor 230b is disposed at the first frame 210, and the first motor 230a pulls the second string 240b in a direction opposite to the direction of pulling the first string 240a from the pulley 250, thereby being able to move the second frame 220.

In an embodiment, the first string 240a and the second string 240b may also be formed of an elastic material or an inextensible material. At this time, the first string 240a and the second string 240b may be either a twist type or a non-twist type.

In another example, by attaching a clutch which changes the respective directions to the two motors, it is possible to perform the control so that the operating directions are the same. Thus, the two motors can also be operated to pull the strings in the opposite directions, but they can be operated to pull the strings in the same direction each other by utilizing the clutch. Thus, by driving the motion control device using two motors, it is possible to provide greater force than the case of driving using a single motor.

Therefore, according to one embodiment of the present invention, there is an advantage that the rigidity of the exoskeleton disposed in the frame becomes stronger when twisting all the two strings. Also, when untwisting all the two strings, mechanical rigidity of the exoskeleton becomes weak. It is also possible to easily measure the force applied from the outside, by utilizing the nature of the twisted string being untwisted in proportion to the force when the external force is applied.

FIG. 13 is a block diagram illustrating a motion control device according to another embodiment of the present invention.

Referring to (a) of FIG. 13, a motion control device 300 of the third embodiment includes a guide 10 formed between the joint and the joint of the body, strings 20a, 20b connected along the guide, and a first motor 30 which is connected to the string and control the string to control a part of the body to move. For example, the guide 10 can be formed between the joint and the joint of the body, and in FIG. 12, the guide 10 is described as being formed between the node and the node of the hand.

The strings 20a, 20b are connected along the guide 10, and the two strings may be used depending on the embodiment. In an embodiment, the string connected along the guide formed in an interior region (palm) of the body is referred to as a first string 20a, and the string connected along the guide formed in an external region (back of the hand) of the body is referred to as a second string 20b.

The strings 20a, 20b can be formed of an elastic material or an inextensible material. At this time, the strings 20a, 20b can be either a twist type or a non-twist type.

The first motor 30 is connected to the strings 20a, 20b and controls the strings 20a, 20b to be able to control a part of the body to move. In an embodiment, the motor can be disposed for each region of the body to be moved. For example, if the body is a hand, one motor can be installed in each finger. That is, since a person has five fingers, five motors can be used.

In another embodiment, at least one motor can be disposed at a plurality of regions according to the direction of the region of the body to be moved. For example, for mittens or those who do not have five fingers, it is also possible to dispose a motor that controls the thumb and to dispose one motor in the remaining fingers. To do this, by placing the two strings, it is possible to make two strings wind and unwind in the different directions from each other, in accordance with the operating direction of the motor.

Therefore, according to the present invention, there is an effect capable of providing great force using a small motor, by directly disposing the motor in the glove, and by pulling the string with the motor.

Referring to (b) of FIG. 13, when the first string 20a is provided in the interior region of the body and the second string 20b is used in the exterior region of the body, this case is to allow the two strings to be wound and unwind in accordance with the operating direction of the motor. For this reason, the motion control device can be configured so that the pulley 60 is disposed between the strings 20a, 20b and the motors 30, 40.

The pulley 60 serves to wind or unwind the strings 20a, 20b, by rotating the string 20a, 20b with the motors 30, 40.

For example, the first string 20a is wound around the pulley 60, and when the first motor 30 pulls the first string 20a, the finger (thumb) is unfolded in an outward direction of the hand, while the first string 20a wound around the pulley 60 is unwound along with the rotation of the pulley 60. In contrast, when the first motor 30 releases the first string 20a which has been pulled, the finger (thumb) is folded in the inward direction of the hand, while the first string 20a is wound around the pulley 60 along with the rotation of the pulley 60.

For example, the second string 20b is wound around the pulley 60, and when the second motor 40 pulls the second string 20b, the fingers (fingers except the thumb) are folded in the inward direction of the hand, while the second string 20b wound around the pulley 60 is unwound along with the rotation of the pulley 60. In contrast, when the second motor 40 releases the second string 20b which has been pulled, the fingers (fingers except the thumb) are unfolded in the outward direction of the hand, while the second string 20b is wound around the pulley 60 along with the rotation of the pulley 60.

At this time, an alternative motor 30a is further disposed on the left side of the second motor 40, but when the first motor 30 is not formed in the palm as in (a), the alternative motor 30a which controls the thumb can also be disposed to the back of the hand, as in (b). That is, the alternative motor 30a can control the motion of the thumb, instead of the first motor 30 of the palm.

In an embodiment, the pulley 60 can be connected to the first string 20a at one end and can be connected to the second string 20b at the other end opposite to the one end. Therefore, the pulley 60 can wind the first string 20a and unwind the second string 20b, or can unwind the first string 20a or wind the second string 20b, according to the direction of motion of the motor.

In this case, it is possible to operate all the first string 20a and the second string 20b by a single motor. For example, when the motor rotates in a normal rotation direction, one end of the pulley 60 can be unwound and the other end can be wound, and when the motor rotates in a reverse rotation direction, one end of the pulley 60 can be wound and the other end can be unwound.

Also, a bidirectional motion exoskeleton type glove may include a support base 50 which fixedly mounts the motors 30, 40 and the pulley 60 onto the body. The support base 50 may be configured by a member capable of being fixedly attached to the body, such as silicon and plastic of a hard material.

Figure 14:
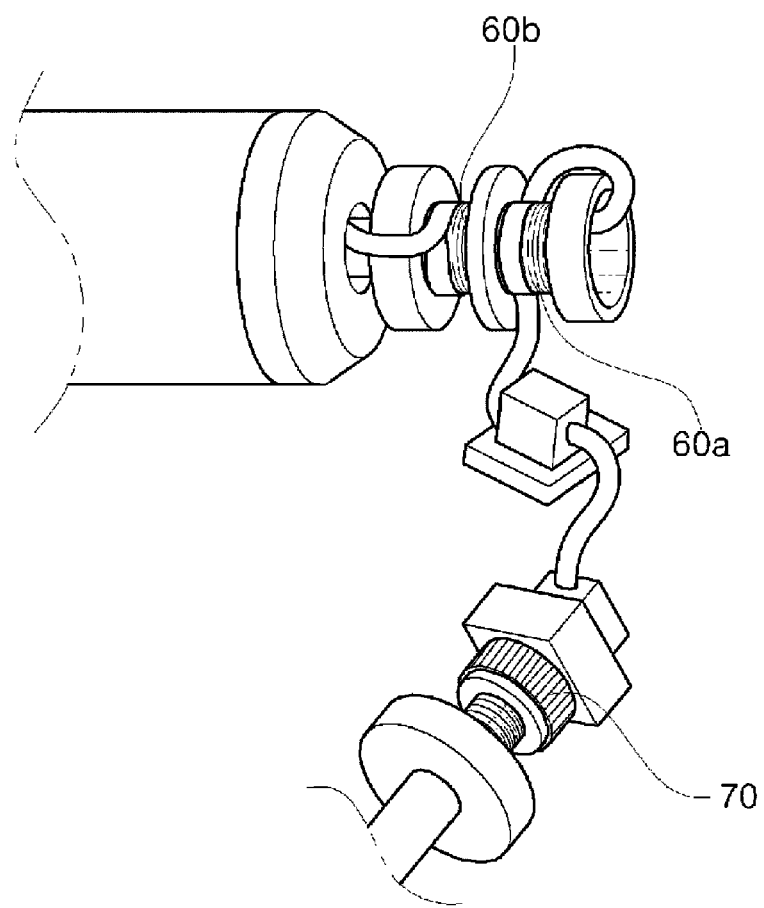
FIGS. 14 and 15 are diagrams illustrating a pulley included in the motion control device according to still another embodiment of the present invention.
Figure 15:
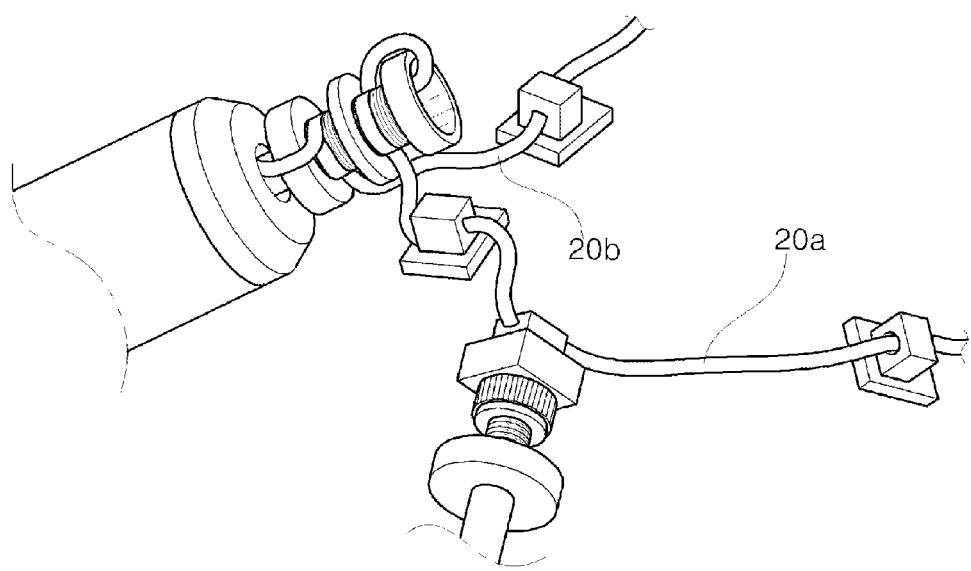

FIGS. 14 and 15 are diagrams illustrating a pulley that is included in the motion control device according to another embodiment of the present invention.

Referring to FIG. 14, a pulley 60 may include two holes 60a, 60b having different diameters or sizes from each other. Referring to FIG. 15, the first hole 60a can rotate the first string 20a, and the second hole 60b can rotate the second string 20b.

In an embodiment, the first hole 60a can wind or unwinding the first string 20a under the control of the first motor 30 which controls the first string 20a. Further, the second hole 60b can wind or unwind second string 20b, under the control of the second motor 40 which controls the second string 20b.

In another embodiment, it is possible to perform the control so that a single motor winds the first string 20a and unwinds the second string 20b or unwinds the first string 20a and winds the second string 20b, by utilizing the two holes 60a, 60b included in the pulley 60.

Also, in FIG. 14, a bidirectional motion exoskeleton type glove can further include a size adjustment unit 70 which is connected to the motor to adjust the length of the string depending on the size of the body. By placing bolts and nuts as the size adjustment unit 70, the bolts and the nuts serve to regulate the length of the string depending on the size of the body. The sizes of bodies are very diverse and different for each object. Therefore, the bidirectional motion exoskeleton type glove can manually adjust the tension by providing the size adjustment unit 70 to adjust the length of the string, depending on the size of the body.

Therefore, according to the present invention, since the motor is attached to the back of the hand or the wrist and is connected along the guide only by the string, the palm is free to easily grasp the article.

Figure 16:
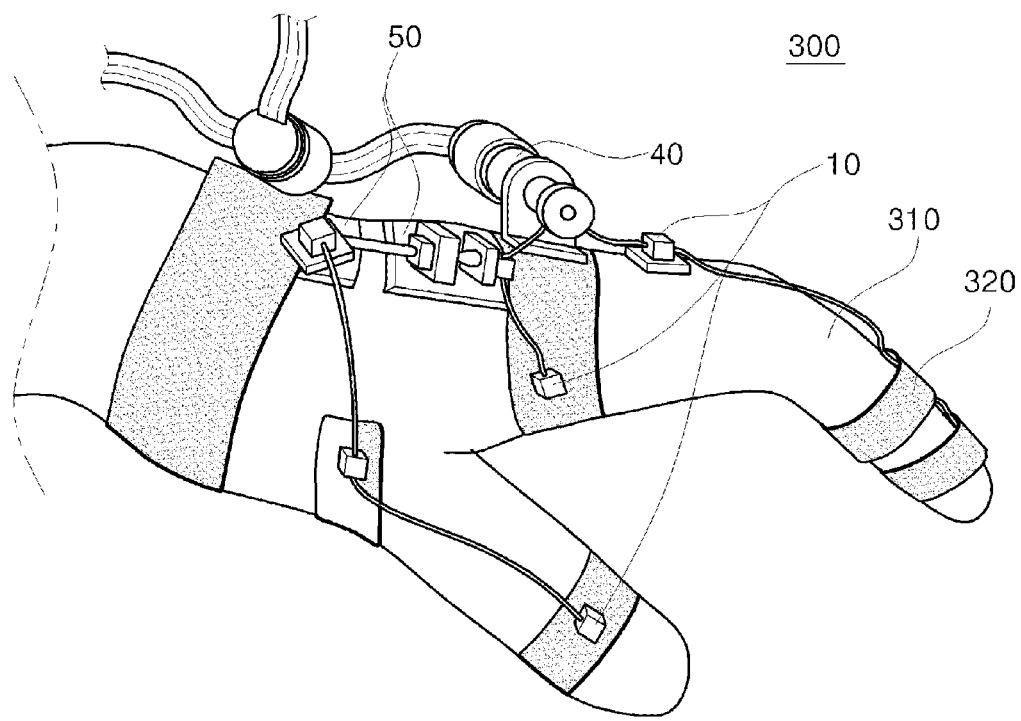
FIG. 16 is a diagram illustrating a side view of a motion control device according to still another embodiment of the present invention.

FIG. 16 illustrates a side view of a motion control device according to another embodiment of the present invention.

Referring to FIG. 16, a motion control device 300 can include a first layer 310 which is in direct contact with the body, a second layer 320 in which a support base and a motor are formed on the first layer 310, and a third layer in which a guide and a string are formed on the second layer 320 and the guide string to control the motion of the body.

Since the first layer 310 is in direct contact with the body, soft materials such as cotton, suede and velvet can be used.

Since the second layer 320 is configured to mount the support based and the motor, and a somewhat rigid material such as rubber material can be used. Otherwise, the second layer 320 may be formed of any one of suede, velvet, silicon, urethane, leather, rubber and cotton.

The third layer can include the guides 10 formed on the inner and outer areas of the body, and the strings formed in the inner and outer areas of the body along the guide 10. For example, a first string 20a is provided in the inner area of the body, and a second string 20b can be used in the outer area of the body. The second motor 40 can control the second string 20b to perform the control such that a part of the body is moved.

Also, the pulley is disposed on the second layer 320 to rotate the strings 20a, 20b by the second motor 40, thereby permitting the strings 20a, 20b to be wound or unwound. Therefore, since the pulley serves as a sheave, it is possible to provide great force by utilizing a small motor that can be directly connected to the body.

INDUSTRIAL APPLICABILITY

In the detailed description of the present invention as described above, specific examples have been described. However, various variations can be made within the limits without departing from the scope of the present invention. Technical idea of the present invention is not to be construed as being limited to the above-mentioned embodiments of the present invention, and it should be defined by not only the scope of the claims but those equivalent to the scope of the claims.

What is claimed is:

1. A motion control device comprising:
   a frame including a first frame and a second frame which supports an exoskeleton of a body;
   a pulley disposed between the first frame and the second frame, wherein the first fame is disposed at a first portion and the second frame is disposed at a second portion, the first and second portions moving in predetermined directions, respectively, with respect to the pulley;
   a motor including a first motor and a second motor both disposed at an opposite side of the pulley with respect to one of the first and the second frames, the first and second motors both being disposed at the one of the first and second frames;
   a string including a first string and a second string, one end of the first string being connected to the pulley and the other end thereof being connected to the first motor, one end of the second string being connected to the pulley and the other end thereof being connected to the second motor; and
   a coupling including a first coupling and a second coupling, the first coupling being disposed between the pulley and the first motor and adjacent to the first motor, and the second coupling being disposed between the pulley and the second motor and adjacent to the second motor, the first coupling having a first rotating shaft in parallel with the first string, and the second coupling having a second rotating shaft in parallel with the second string, wherein the first coupling is configured to rotate to twist the first by rotation of the first motor and the second coupling is configured to rotate to untwist the second string by rotation of the second motor, or vice versa.

2. The motion control device of claim 1, wherein one side of the frame includes a connecting portion formed in the form of having two parts engaged with each other.

3. The motion control device of claim 1, further comprising:
   a separator which is disposed between the motor and the pulley to separate the first string and the second string from each other.

4. The motion control device of claim 1, further comprising:
   a gear operation unit which is connected to the motor to operate an operating direction of the motor;
   wherein the coupling is rotated in a forward direction or a backward direction to twist or untwist the string in accordance with the operating direction which is operated by the gear operation unit.

5. The motion control device of claim 1, wherein the pulley includes a first hole connected to the first string and a second hole connected to the second string,
   wherein the first string is twisted and the second string is untwisted, or vice versa, using the first hole and the second hole.

* * * * *